United States Patent
Feldman

(10) Patent No.: US 11,357,428 B2
(45) Date of Patent: Jun. 14, 2022

(54) TRANSCUTANEOUS SENSOR WITH DUAL ELECTRODES AND METHODS OF DETECTING AND COMPENSATING FOR WITHDRAWAL OF A TRANSCUTANEOUS SENSOR FROM A PATIENT

(71) Applicant: ABBOTT DIABETES CARE INC., Alameda, CA (US)

(72) Inventor: Benjamin Feldman, Alameda, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 513 days.

(21) Appl. No.: 16/174,138

(22) Filed: Oct. 29, 2018

(65) Prior Publication Data
US 2019/0125230 A1   May 2, 2019

Related U.S. Application Data

(60) Provisional application No. 62/578,883, filed on Oct. 30, 2017.

(51) Int. Cl.
*A61B 5/1486* (2006.01)
*A61B 5/145* (2006.01)

(52) U.S. Cl.
CPC ...... *A61B 5/14865* (2013.01); *A61B 5/14532* (2013.01)

(58) Field of Classification Search
CPC ............ A61B 5/14865; A61B 5/14532; A61B 5/7221; A61B 5/1495; A61B 2560/0223; A61B 5/6843; A61B 5/6844
See application file for complete search history.

(56) References Cited

U.S. PATENT DOCUMENTS

| 4,655,880 A | 4/1987 | Liu |
| 2010/0081906 A1* | 4/2010 | Hayter ............... A61B 5/1451 600/347 |
| 2011/0319734 A1* | 12/2011 | Gottlieb ............ A61B 5/14532 600/347 |
| 2015/0099954 A1 | 4/2015 | Achmann et al. |
| 2018/0042557 A1* | 2/2018 | Park ................... A61B 5/6831 |

FOREIGN PATENT DOCUMENTS

WO   WO2012/089505 A1   7/2012

OTHER PUBLICATIONS

International Search Report and Written Opinion issued in corresponding application No. PCT/US2018/058047, dated Feb. 12, 2019, 13 pages.

* cited by examiner

*Primary Examiner* — Sean P Dougherty
*Assistant Examiner* — Kyle W. Kretzer
(74) *Attorney, Agent, or Firm* — Lewis Roca Rothgerber Christie LLP

(57) ABSTRACT

A transcutaneous sensor configured to measure one or more physiological conditions of a patient. The transcutaneous sensor includes a substrate and first and second working electrodes on the substrate. The first working electrode includes a first active sensing area and the second working electrode includes a second active sensing area. The first active sensing area of the first working electrode is longitudinally offset along the substrate from the second active sensing area of the second working electrode.

19 Claims, 8 Drawing Sheets

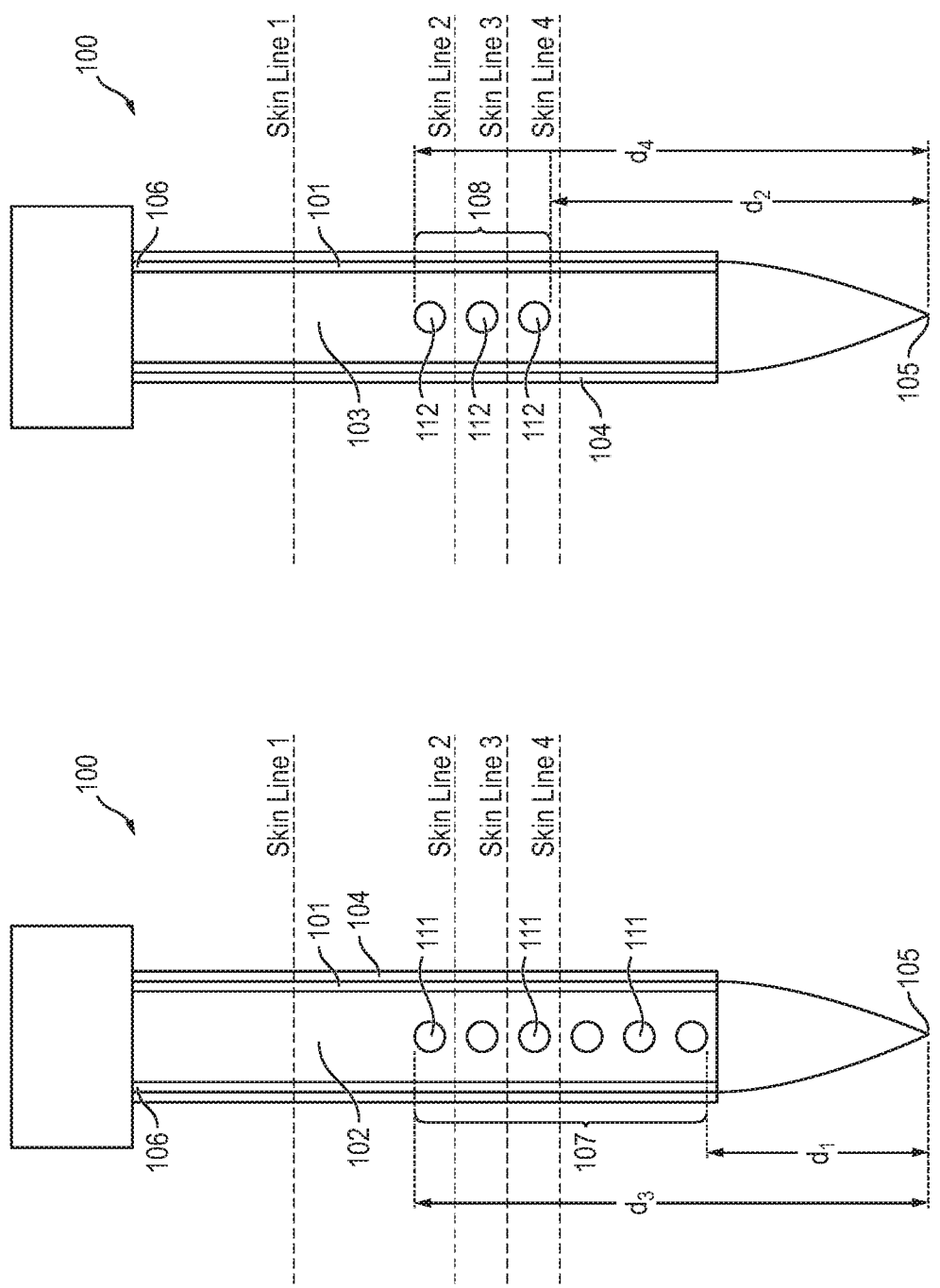

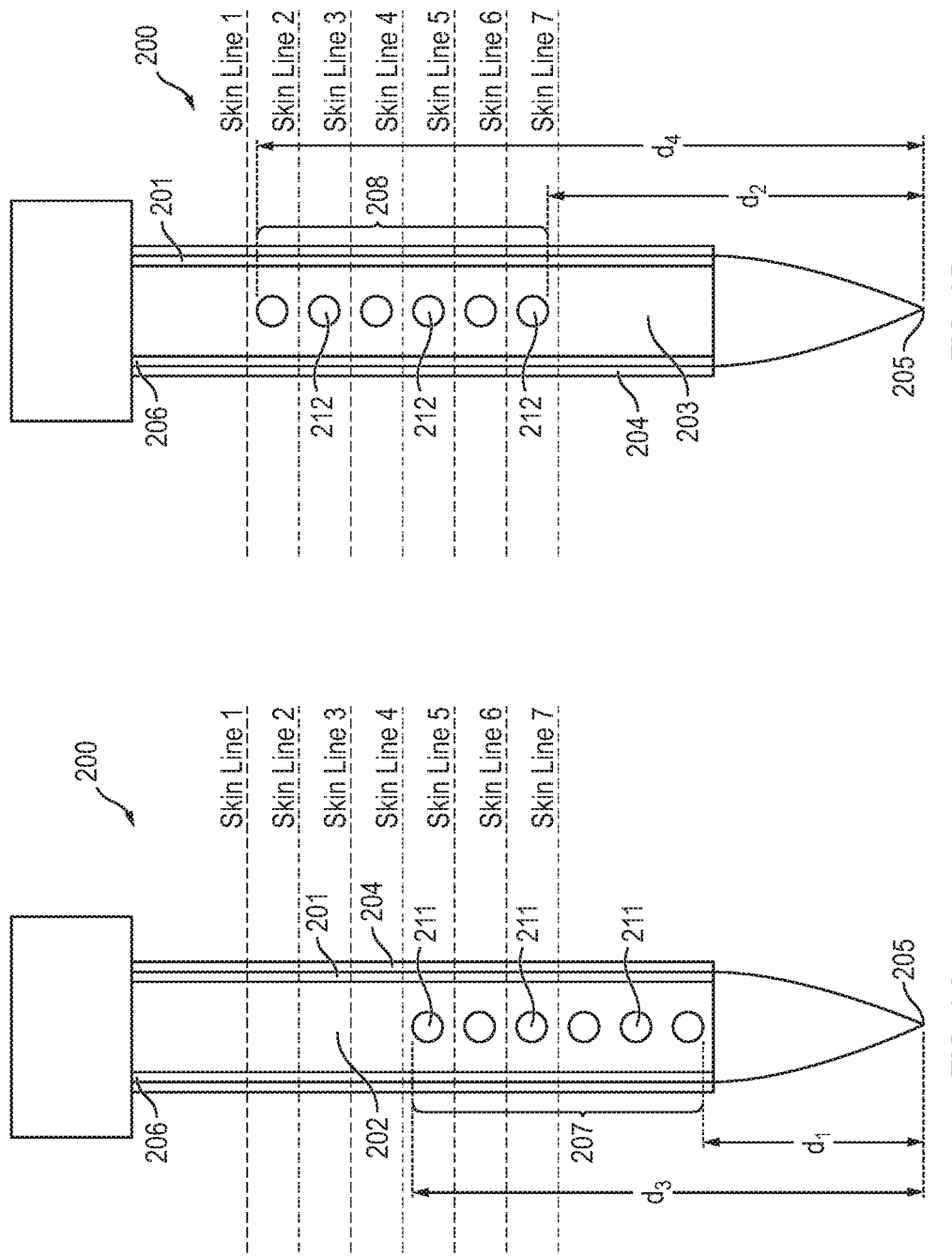

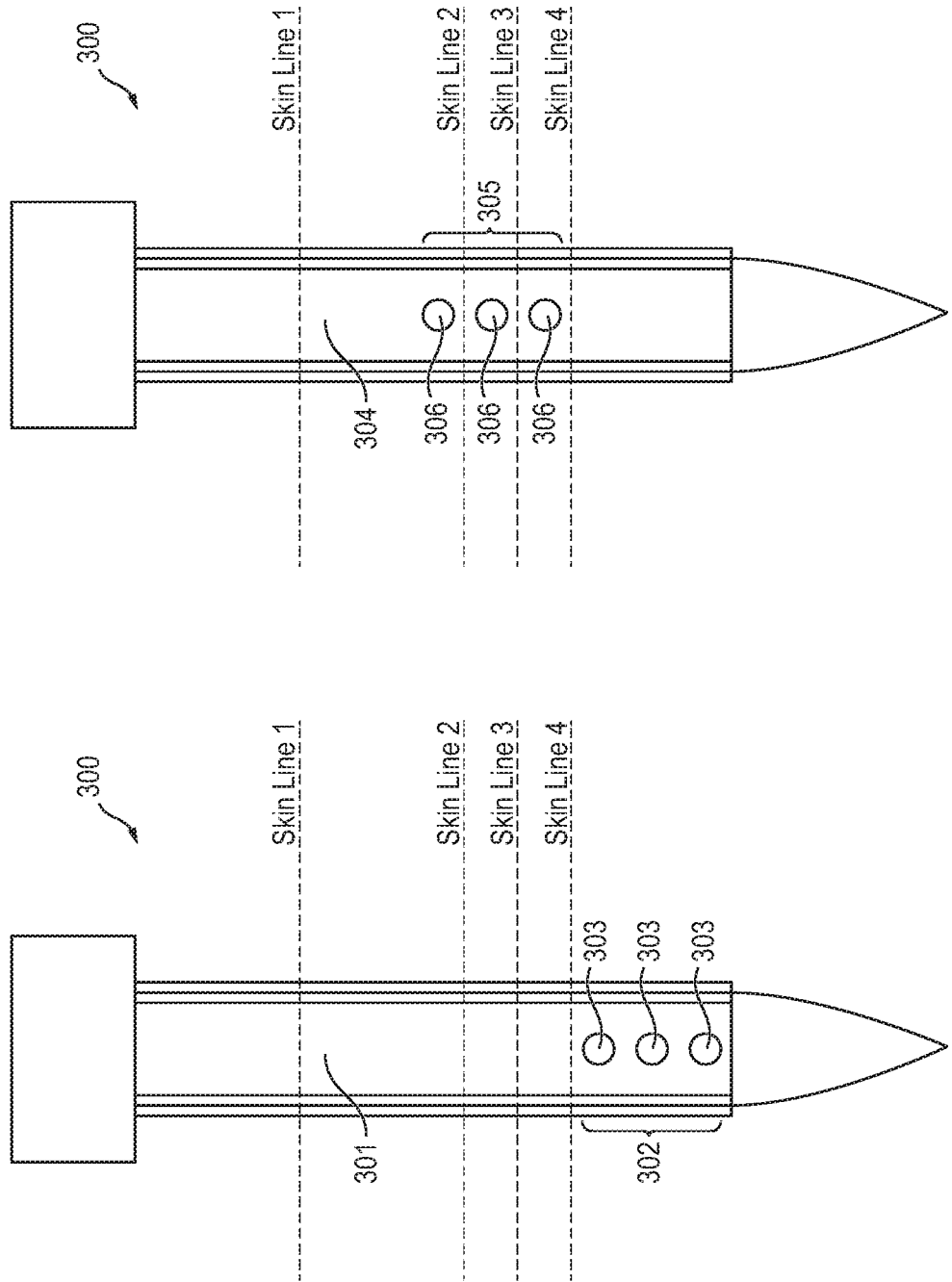

TRANSCUTANEOUS SENSOR WITH DUAL ELECTRODES AND METHODS OF DETECTING AND COMPENSATING FOR WITHDRAWAL OF A TRANSCUTANEOUS SENSOR FROM A PATIENT

CROSS-REFERENCE TO RELATED APPLICATION

This application claims the benefit of and priority to U.S. Provisional application No. 62/578,883, "TRANSCUTANEOUS SENSOR WITH DUAL ELECTRODES AND METHODS OF DETECTING AND COMPENSATING FOR WITHDRAWAL OF A TRANSCUTANEOUS SENSOR FROM A PATIENT," filed Oct. 30, 2017, the entire content of which is incorporated herein by reference.

FIELD

The present disclosure relates generally to transcutaneous sensors.

BACKGROUND

Transcutaneous sensors are configured to be implanted in a patient and may be utilized to determine a variety of different conditions, such as blood glucose levels, which are important for diabetes management. Related art transcutaneous sensors, however, are prone to withdraw from the patient's skin after insertion if, for example, a unidirectional force is applied to an external on-body sensor mount supporting the sensor. For instance, if the patient lays on the external sensor mount in such a way to consistently push the sensor in a direction away from the patient's body, the transcutaneous sensor may slowly withdraw from the patient's body over the course of days or weeks.

When the external sensor mount moves away from the patient's body, at least a portion of the active sensing area of the transcutaneous sensor may be withdrawn from the patient's body. This phenomenon is known as "pullout." Pullout of the active sensing area of the sensor affects the sensor output signal. If the withdrawal of the active sensor area from the patient's body is complete, the sensor output signal (e.g., current output) falls to zero. Detecting that the sensor has completely withdrawn from the patient's body may be simple because, for example, in the case of measuring blood glucose levels, zero current is not an expected physiologically result.

If the withdrawal of the sensor is partial, the sensor output signal can be reduced to a non-zero value, such as 50% of the signal expected for a fully implanted sensor. Accordingly, partial withdrawal can be difficult to detect because the results can still appear physiologically reasonable, especially in the absence of reference blood analyte values (e.g., a factory calibrated sensor). Accordingly, the undetected partial withdrawal of a transcutaneous sensor from a patient may lead to reporting artificially depressed sensor signals (e.g., artificially depressed blood glucose values) to the patient.

SUMMARY

The present disclosure is directed to various embodiments of a transcutaneous sensor configured to measure one or more physiological conditions of a patient. In one embodiment of the present disclosure, the transcutaneous sensor includes a substrate and first and second working electrodes on the substrate. The first working electrode includes a first active sensing area and the second working electrode includes a second active sensing area. The first active sensing area of the first working electrode is longitudinally offset along the substrate from the second active sensing area of the second working electrode. By including the first and second working electrodes with the longitudinal offset, the sensor is capable of detecting withdrawal (e.g., pullout) of the sensor from the patient as the respective output signals of the first and second working electrodes do not change identically in response to withdrawal of the sensor. For example, if the ratio of the respective output signals of the first and second working electrodes is different than the size ratio of the respective sizes of the first and second active areas of the first and second working electrodes, it can be determined that the sensor has at least partially withdrawn from the patient and the output signals of the sensor may be corrected accordingly.

The working electrodes may be arranged in any suitable manner on the substrate. For example, the first working electrode may be on a first side of the substrate and the second working electrode may be on a second side of the substrate opposite the first side.

The withdrawal of the sensor may be determined according to the respective sizes of the active sensing areas of the first and second working electrodes. For example, the first active sensing area may have a first size and the second active sensing area may have a second size different than the first size. In some embodiments, the first active sensing area may have a first size and the second active sensing area may have a second size substantially equal to the first size.

The first active sensing area may include a first series of sensing spots and the second active sensing area may include a second series of sensing spots. A size of each sensing spot of the first series of sensing spots may be substantially the same as a size of each sensing spot of the second series of sensing spots. The first series of sensing spots may include a greater number of sensing spots than the second series of sensing spots.

A proximalmost end of the first active sensing area may be spaced apart from the distal end of the substrate by a first distance and a proximalmost end of the second active sensing area may be spaced apart from the distal end of the substrate by a second distance different than the first distance. A distalmost end of the first active sensing area may be spaced apart from the distal end of the substrate by a first distance and a distalmost end of the second active sensing area may be spaced apart from the distal end of the substrate by a second distance different than the first distance. A longitudinally centered portion of the first active sensing area may be offset from a longitudinally centered portion of the second active sensing area.

The transcutaneous sensor may include a reference electrode on the substrate. The transcutaneous sensor may also include a counter electrode on the substrate. The transcutaneous sensor may include a first dielectric insulator layer between the reference electrode and the substrate, and a second dielectric insulator layer between the counter electrode and the substrate.

The first active sensing area and the second active sensing area may include an analyte-specific enzyme and an electron transfer agent. The first active sensing area and the second active sensing area may also include a cross linker. The analyte-specific enzyme may be glucose oxidase. The electron transfer agent may be a redox polymer.

The transcutaneous sensor may also include a membrane overlaying the first and second active sensing areas.

The present disclosure is also directed to various methods of detecting the withdrawal of a transcutaneous sensor from a patient. In one embodiment of the present disclosure, the method includes determining a current ratio of a first current output by a first working electrode of the transcutaneous sensor to a second current output by a second working electrode of the transcutaneous sensor. The method also includes comparing the current ratio to a size ratio defined by a first size of a first active sensing area of the first working electrode to a second size of a second active sensing area of the second working electrode. The method further includes determining, if the current ratio is different than the size ratio, that the transcutaneous sensor has at least partially withdrawn from the patient. The method may also include compensating for a reduction in the current output by one of the first and second working electrodes due to the partial withdrawal of the transcutaneous sensor using a difference between the current ratio and the size ratio.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

FIGS. 1A-1D are a plan view, a side detailed view, a front detailed view, and a back detailed view, respectively, of a transcutaneous sensor according to one embodiment of the present disclosure;

FIGS. 2A-2B are a front view and a back view, respectively, of a transcutaneous sensor according to another embodiment of the present disclosure;

FIGS. 3A-3B are a front view and a back view, respectively, of a transcutaneous sensor according to another embodiment of the present disclosure;

DETAILED DESCRIPTION

Figure 1A:
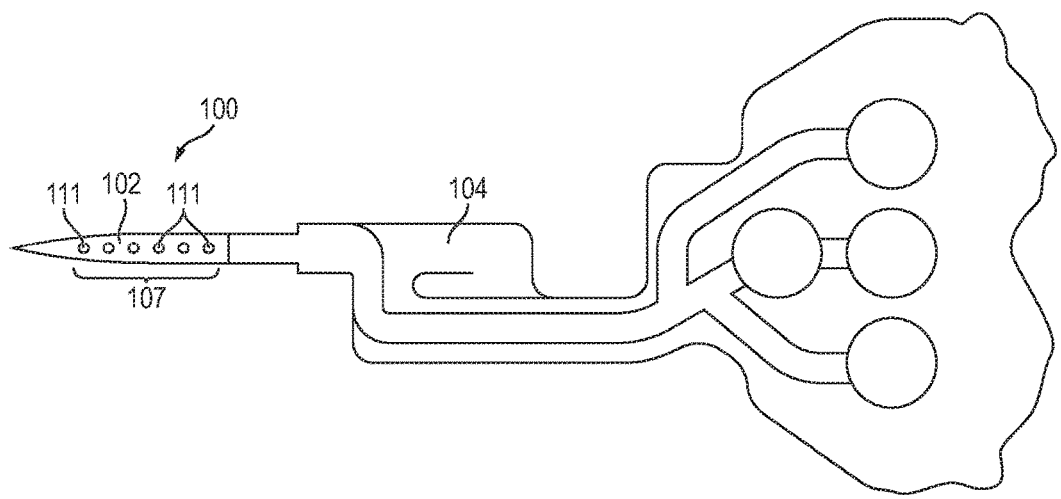

The present disclosure is directed to various embodiments of transcutaneous sensors. The transcutaneous sensors of the present disclosure are configured to be inserted under a patient's skin to measure one or more physiological conditions, such as the patient's blood glucose levels. The transcutaneous sensor as disclosed herein, measures the concentration of an analyte (e.g., glucose) corresponding to a physiological condition. The transcutaneous sensor according to one or more embodiments of the present disclosure includes a pair of working electrodes that are configured to detect when the transcutaneous sensor has at least partially withdrawn from the patient. Additionally, the pair of working electrodes are configured to permit the sensor to compensate for a reduction in the sensor output signal (e.g., current output) of one of the working electrodes due to the partial withdrawal of the sensor from the patient, which might otherwise result in an artificially depressed measurement being reported to the patient.

As used herein, a "working electrode" is an electrode at which the analyte (or a second compound whose level depends on the level of the analyte) is electrooxidized or electroreduced with or without the agency of an electron transfer agent.

As used herein, a "counter electrode" refers to an electrode paired with the working electrode, through which passes a current equal in magnitude and opposite in sign to the current passing through the working electrode. In the context of embodiments of the present disclosure, the term "counter electrode" includes both a) counter electrodes and b) counter electrodes that also function as reference electrodes (i.e., counter/reference electrodes), unless otherwise indicated.

As used herein, a "reference electrode" includes both a) reference electrodes and b) reference electrodes that also function as counter electrodes (i.e., counter/reference electrodes), unless otherwise indicated.

As used herein, "electrolysis" is the electrooxidation or electroreduction of a compound either directly at an electrode or via one or more electron transfer agents.

As used herein, components are "immobilized" within a sensor, for example, when the components are entrapped on or covalently, ionically, or coordinatively bound to constituents of the sensor and/or are entrapped in a polymeric or sol-gel matrix or membrane which precludes mobility.

As used herein an "electron transfer agent" is a compound that carries electrons between the analyte and the working electrode, either directly, or in cooperation with other electron transfer agents. One example of an electron transfer agent is a redox mediator or red.

As used herein, a "redox mediator" is an electron-transfer agent for carrying electrons between an analyte, an analyte-reduced or analyte-oxidized, enzyme, and an electrode, either directly, or via one or more additional electron-transfer agents. A redox mediator that includes a polymeric backbone may also be referred to as a "redox polymer".

As used herein, an "active sensing area" and a "sensing area" are used interchangeably to refer to a component of the sensor which includes constituents that facilitate the electrolysis of the analyte. The sensing area may include constituents such as an electron transfer agent (e.g., a redox mediator or a redox polymer), a catalyst (e.g., an analyte-specific enzyme) which catalyzes a reaction of the analyte to produce a response at the working electrode, or both an electron transfer agent and a catalyst. In some embodiments, a sensor includes a sensing area that is non-leachably disposed in proximity to, or on, the working electrode. In some embodiments, the sensing area includes an analyte specific enzyme, an electron transfer agent, and a cross-linker.

With reference now to FIGS. 1A-1D, a transcutaneous sensor 100 according to one embodiment of the present disclosure includes a substrate 101, a first working electrode 102 on the substrate 101, a second working electrode 103 on the substrate 101, and a sensor membrane 104 covering the substrate 101 and the first and second working electrodes 102, 103. Although in the illustrated embodiment the first and second working electrodes 102, 103 are positioned on opposite sides of the substrate 101, in one or more embodiments the first and second working electrodes 102, 103 may be positioned in any other suitable locations on the substrate 101. For example, in one or more embodiments, the first and second working electrodes 102, 103 may be on the same side of the substrate 101. The substrate 101 includes a distal end 105 configured to be inserted into the skin of a patient and a proximal end 106 opposite the distal end 105 configured to be connected to various electrical connections for transmitting the output signals of the transcutaneous sensor 100. The distal end 105 may have a pointed or rounded tip, or other shaped tip that facilitates insertion of the sensor 100 into the patient's skin.

Figure 1B:
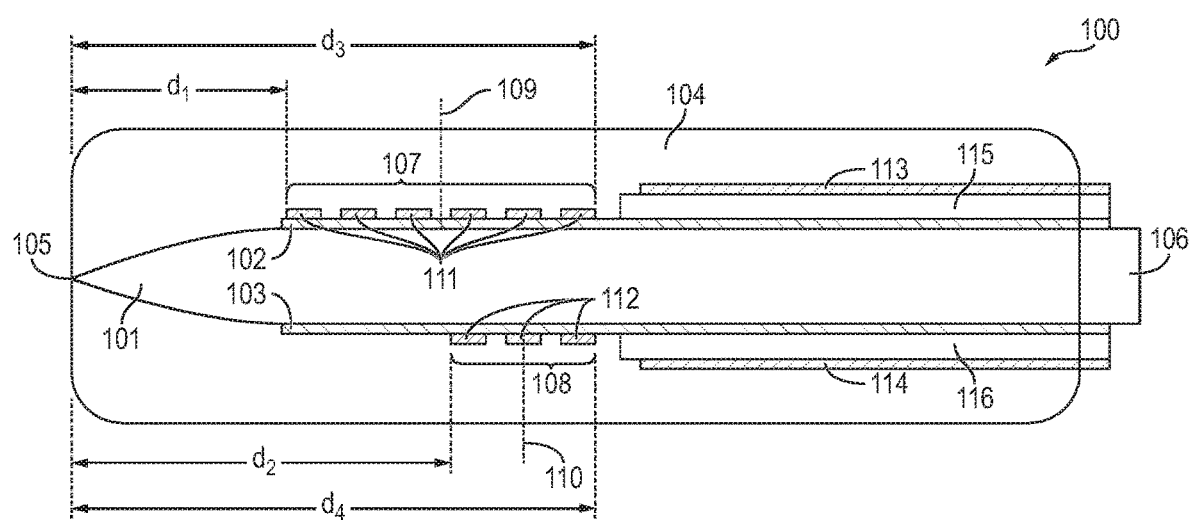

With continued reference to the embodiment illustrated in FIGS. 1B-1D, the first working electrode 102 includes a first active sensing area 107 and the second working electrode 103 includes a second active sensing area 108. Although not shown in the drawings, the first active sensing area 107 of the first working electrode 102 is configured to transduce an analyte signal into a first output signal ($i_1$) (e.g., a current output signal) and the second active sensing area 108 of the second working electrode 103 is configured to transduce an analyte signal into a second output signal ($i_2$) (e.g., a current output signal). The output signals ($i_1$, $i_2$) of the first and second active sensing areas 107, 108 correspond to a physiological condition of the patient, such as, for instance, the blood glucose level of the patient. Additionally, in the illustrated embodiment, the first active sensing area 107 of the first working electrode 102 has a first area ($a_1$) and the second active sensing area 108 of the second working electrode 103 has a second area ($a_2$).

The first active sensing area 107 of the first working electrode 102 is longitudinally offset along the substrate 101 from the second active sensing area 108 of the second working electrode 103. In the illustrated embodiment, a distalmost end of the first active sensing area 107 is spaced apart from the distal end 105 of the substrate 101 by a first distance $d_1$ and a distalmost end of the second active sensing area 108 is spaced apart from the distal end 105 of the substrate 101 by a second distance $d_2$ greater than the first distance $d_1$ (i.e., the distalmost end of the second active sensing area 108 is spaced apart from the distal end 105 of the substrate 101 by a greater distance than the distalmost end of the first active sensing area 107). Additionally, in the illustrated embodiment, a proximalmost end of the first active sensing area 107 is spaced apart from the distal end 105 of the substrate by a third distance $d_3$ and a proximalmost end of the second active sensing area 108 is spaced apart from the distal end 105 of the substrate 101 by a fourth distance $d_4$ that is equal or substantially equal to the third distance $d_3$ (i.e., the proximalmost ends of the first and second active sensing areas 107, 108 are spaced apart from the distal end 105 of the substrate 101 by the same or substantially the same distance). Accordingly, in the illustrated embodiment, a longitudinally central portion 109 of the first active sensing area 107 is offset from a longitudinally central portion 110 of the second active sensing area 108. In one or more embodiments, the proximalmost end of the first active sensing area 107 may not be aligned with the proximalmost end of the second active sensing area 108.

Additionally, in the illustrated embodiment, the first area $a_1$ of the first active sensing area 107 is greater than the second area $a_2$ of the second active sensing area 108. In the illustrated embodiment, the first and second active sensing areas 107, 108 each include a series of discrete sensing spots 111, 112 (e.g., dots), respectively. In the illustrated embodiment, the size of each of the discrete sensing spots 111 in the first active sensing area 107 is equal or substantially equal to the size of each of the discrete sensing spots 112 in the second active sensing area 108. In the illustrated embodiment, the number of discrete sensing spots 111 in the first active sensing area 107 is greater than the number of discrete spots 112 in the second active sensing area 108. Although in the illustrated embodiment there are six uniformly sized discrete sensing spots 111 in the first active sensing area 107 and three uniformly sized discrete sensing spots 112 in the second active sensing area 108, in one or more embodiments, the first and second active sensing areas 107, 108 may include any other suitable number of discrete sensing spots. Additionally, in one or more embodiments, the first active sensing area 107 and/or the second active sensing area 108 may include a continuous strip (e.g., an elongated ellipse) rather than a series of discrete sensing spots. Furthermore, in one or more embodiments, the first area $a_1$ of the first active sensing area 107 may be equal or substantially equal to the second area $a_2$ of the second active sensing area 108.

Additionally, in one or more embodiments, transcutaneous sensor 100 may include a reference electrode, a counter electrode, or counter-reference electrodes. In the illustrated embodiment, the transcutaneous sensor 100 includes a counter electrode 113 and a reference electrode 114. In the illustrated embodiment, the reference electrode 114 and the counter electrode 113 are on opposite sides of the substrate 101. Additionally, in the illustrated embodiment, the counter electrode 113 is separated from the first working electrode 102 by a first dielectric insulator layer 115 and the reference electrode 114 is separated from the second working electrode 103 by a second dielectric insulator layer 116.

When the sensor 100 is fully implanted such that the first and second active sensing areas 107, 108 are completely below the skin line of the patient (shown as "skin line 1" in FIGS. 1C-1D), the ratio of the first and second output signals ($i_1/i_2$) is equal to the ratio of the first and second areas ($a_1/a_2$) of the first and second active sensing areas 107, 108 (i.e., an equilibrium in which $i_1/i_2=a_1/a_2$ is achieved when the first and second active sensing areas 107, 108 are completely below the skin line of the patient). In the illustrated embodiment, when the sensor 100 is fully embedded below the skin line, the ratio of the first and second output signals ($i_1/i_2$) is equal to 2 because the area of the first active sensing area 107 is twice as large as the area of the second active sensing area 108 (i.e., $a_1/a_2=2$).

As the sensor 100 is withdrawn from the patient's skin such that the proximalmost discrete sensing spot 111, 112 of each of the first and second active sensing areas 107, 108 is withdrawn from the patient's skin (shown as "skin line 2" in FIGS. 1B-1C), the ratio of the first and second output signals ($i_1/i_2$) increases to 2.5, which exceeds the equilibrium value of 2. This increase in the ratio of the first and second output signals ($i_1/i_2$) above the equilibrium value is indicative of a partial pullout of the sensor 100. Additionally, the increase in the ratio of the first and second output signals ($i_1/i_2$) may also be utilized to correct the first output signal ($i_1$) of the first working electrode 102, which has been artificially depressed due to the withdrawal of the proximalmost discrete sensing spot 111 of the first active sensing area 107. For example, in the illustrated embodiment, the increase in the ratio of the first and second output signals ($i_1/i_2$) to 2.5 from an equilibrium value of 2 indicates that the output signal ($i_1$) (e.g., the output current) of the first working electrode 102 needs to be corrected by +20% to compensate for the reduction in the output signal ($i_1$) due to the partial withdrawal. That is, because one of the six discrete sensing spots 111 has withdrawn from the patient's skin, the first active sensing area 107 generates an output signal ($i_1$) that has been artificially depressed to 5/6 and therefore the output signal ($i_1$) needs to be corrected by a factor of 6/5 (i.e., 1.2 or 20%) to compensate for the reduction in the output signal ($i_1$) due to the partial withdrawal. The present disclosure is not limited to correcting an output signal when there has been complete withdrawal of one or more of the discrete sensing spots, and instead can also be used to correct an output signal when there has been partial withdrawal of one or more of the discrete sensing spots.

As the sensor 100 continues to withdraw from the patient's skin such that the two proximalmost discrete sensing spots 111, 112 of each of the first and second active sensing areas 107, 108 are withdrawn from the patient's skin (shown as "skin line 3" in FIGS. 1C-1D), the ratio of the first and second output signals ($i_1/i_2$) increases to 4, which exceeds the equilibrium value of 2. This increase in the ratio of the first and second output signals ($i_1/i_2$) above the equilibrium value is indicative of further partial pullout of the sensor 100. Additionally, in the illustrated embodiment, the increase in the ratio of the first and second output signals ($i_1/i_2$) to 4 from an equilibrium value of 2 indicates that the output signal (e.g., the output current) of the first working electrode 102 needs to be corrected by +50% to compensate for the reduction in the output signal due to the further partial withdrawal. That is, because two of the six discrete sensing spots 111 have withdrawn from the patient's skin, the first active sensing area 107 generates an output signal ($i_1$) that has been artificially depressed to 4/6 and therefore the output signal ($i_1$) needs to be corrected by a factor of 6/4 (i.e., 1.5 or 50%).

As the sensor 100 continues to withdraw from the patient's skin such that the three proximalmost discrete sensing spots 111 of the first active sensing area 107 and all three of the discrete sensing spots 112 of the second active sensing area 108 are withdrawn from the patient's skin (shown as "skin line 4" in FIGS. 1C-1D), the ratio of the first and second output signals ($i_1/i_2$) increases to infinity, which indicates pullout of the sensor 100 but does not permit correction of the first output signal of the first working electrode 102. Accordingly, in one or more embodiments, the output signal ($i_1$) (e.g., the output current) of the first working electrode 102 may be corrected as long as the output signal of the second working electrode 103 is non-zero (i.e., as long as at least a portion of the second active area 108 of the second working electrode 103 is below the patient's skin line).

In this manner, the offset configuration of the first and second active sensing areas 107, 108 of the first and second working electrodes 102, 103 is configured to facilitate detection of the partial withdrawal of the transcutaneous sensor 100 from the patient's skin and to facilitate correction of the output signal of one of the working electrodes 102, 103 that had been artificially depressed due to the partial withdrawal of the transcutaneous sensor 100. Table 1 below summarizes the ratio of the first and second output signals ($i_1/i_2$) and the correction to the first output signal ($i_1$) as a function of skin position.

TABLE 1

| Skin position | $i_1/i_2$ | Implied Correction to $i_1$ |
|---|---|---|
| Skin line 1 | 2 | 0% |
| Skin line 2 | 2.5 | +20% |
| Skin line 3 | 4 | +50% |
| Skin line 4 or below | Very large | Not possible |

With reference now to FIGS. 2A-2B, a transcutaneous sensor 200 according to another embodiment of the present disclosure includes a substrate 201, a first working electrode 202 on the substrate 201, a second working electrode 203 on the substrate 201, and a sensor membrane 204 covering the substrate 201 and the first and second working electrodes 202, 203. Although in the illustrated embodiment the first and second working electrodes 202, 203 are positioned on opposite sides of the substrate 201, in one or more embodiments the first and second electrodes 202, 203 may be positioned in any other suitable locations on the substrate 201. For example, in one or more embodiments, the first and second working electrodes 202, 203 may be on the same side of the substrate 201. The substrate 201 includes a distal end 205 configured to be inserted into the skin of a patient and a proximal end 206 opposite the distal end 205 configured to be connected to various electrical connections for transmitting the output signals of the transcutaneous sensor 200.

With continued reference to the embodiment illustrated in FIGS. 2A-2B, the first working electrode 202 includes a first active sensing area 207 and the second working electrode 203 includes a second active sensing area 208. Although not shown in the drawings, the active sensing area 207 of the first working electrode 202 is configured to transduce an analyte signal into a first output signal ($i_1$) (e.g., a current output signal) and the active sensing area 208 of the second working electrode 203 is configured to transduce an analyte signal into a second output signal ($i_2$) (e.g., a current output signal). The output signals ($i_1, i_2$) of the first and second active sensing areas 207, 208 correspond to a physiological condition of the patient, such as, for instance, the blood glucose level of the patient. Additionally, in the illustrated embodiment, the first active sensing area 207 of the first working electrode 202 has a first area ($a_1$) and the second active sensing area 208 of the second working electrode 203 has a second area ($a_2$).

The first active sensing area 207 of the first working electrode 202 is longitudinally offset from the second active sensing area 208 of the second working electrode 203. In the illustrated embodiment, a distalmost end of the first active sensing area 207 is spaced apart from the distal end 205 of the substrate 201 by a first distance $d_1$ and a distalmost end of the second active sensing area 208 is spaced apart from the distal end 205 of the substrate 201 by a second distance $d_2$ greater than the first distance $d_1$ (i.e., the distalmost end of the second active sensing area 208 is spaced apart from the distal end 205 of the substrate 201 by a greater distance than the distalmost end of the first active sensing area 207). Additionally, in the illustrated embodiment, a proximalmost end of the first active sensing area 207 is spaced apart from the distal end 205 of the substrate 201 by a third distance $d_3$ and a proximalmost end of the second active sensing area 208 is spaced apart from the distal end 205 of the substrate 201 by a fourth distance $d_4$ greater than the third distance $d_3$ (i.e., the proximalmost end of the second active sensing area 208 is spaced apart from the distal end 205 of the substrate 201 by a greater distance than the proximalmost end of the first active sensing area 207). That is, in the illustrated embodiment, the second active sensing area 208 is shifted proximally along the substrate 201 relative to the first active sensing area 207. Accordingly, in the illustrated embodiment, a longitudinally central portion 209 of the first active sensing area 207 is offset from a longitudinally central portion 210 of the second active sensing area 208.

Additionally, in the illustrated embodiment, the first area $a_1$ of the first active sensing area 207 is equal or substantially equal to the second area $a_2$ of the second active sensing area 208. In the illustrated embodiment, the first and second active sensing areas 207, 208 each include a series of discrete sensing spots 211, 212 (e.g., dots), respectively. In the illustrated embodiment, the number of discrete sensing spots 211 in the first active sensing area 207 is equal to the number of discrete sensing spots 212 in the second active sensing area 208. Although in the illustrated embodiment there are six uniformly sized discrete sensing spots 211, 212 in each of the first and second active sensing areas 207, 208, respectively, the first and second active sensing areas 207, 208 may include any other suitable number of discrete sensing spots. Additionally, in one or more embodiments, the first active sensing area 207 and/or the second active sensing area 208 may include a continuous strip (e.g., an elongated ellipse) rather than a series of discrete sensing spots.

Additionally, in one or more embodiments, transcutaneous sensor 200 may include a reference electrode, a counter electrode, or counter-reference electrodes. In one or more embodiments, the transcutaneous sensor 200 may include a counter electrode and a reference electrode on opposite sides of the substrate 201, the counter electrode may be separated from the first working electrode 202 by a first dielectric insulator layer, and the reference electrode may be separated from the second working electrode 203 by a second dielectric insulator layer.

When the sensor 200 is fully implanted such that the first and second active sensing areas 207, 208 are completely below the skin line of the patient (shown as "skin line 1" in FIGS. 2A-2B), the ratio of the first and second output signals $(i_1/i_2)$ is equal to the ratio of the first and second areas $(a_1/a_2)$ of the first and second active sensing areas 207, 208 (i.e., an equilibrium in which $i_1/i_2=a_1/a_2$ is achieved when the first and second active sensing areas 207, 208 are completely below the skin line of the patient). In the illustrated embodiment, when the sensor 200 is fully implanted, the ratio of the first and second output signals $(i_1/i_2)$ is equal to 1 because the area $a_1$ of the first active sensing area 207 is equal to the area $a_2$ of the second active sensing area 208 (i.e., $a_1/a_2=1$).

As the sensor 200 is withdrawn from the patient's skin to the position labeled "skin line 2" in FIGS. 2A-2B, the first active sensing area 207 of the first working electrode 202 remains completely inserted below the skin line, but the proximalmost discrete sensing spot 212 of the second active sensing area 208 is withdrawn from the patient's skin. Accordingly, the current $(i_2)$ of the second working electrode 203 falls before the current $(i_1)$ of the first working electrode 202 and the ratio of the first and second output signals $(i_1/i_2)$ increases to 1.2 (i.e., 6/5), which exceeds the equilibrium value of 1. This increase in the ratio of the first and second output signals $(i_1/i_2)$ above the equilibrium value is indicative of a partial pullout of the sensor 200. No correction to the output signal (e.g., output current) of the first working electrode 202 is required at this position because the first active sensing area 207 of the first working electrode 202 remains fully inserted into the patient's skin. In the illustrated embodiment, the first and second active areas 207, 208 are positioned such that the first active sensing area 207 remains fully inserted into the patient's skin up until the position labeled "skin line 4" in FIGS. 2A-2B, at which point the ratio of the first and second output signal $(i_1/i_2)$ is equal to 2 (i.e., six spots 211 of the first active sensing area 207 divided by three spots 212 of the second active sensing area 208 that remain inserted into the patient's skin). Accordingly, in the illustrated embodiment, compensation to the output signal $(i_1)$ of the first working electrode 202 due to the partial withdrawal of the transcutaneous sensor 200 does not need to occur until the ratio of the first and second output signals $(i_1/i_2)$ exceeds 2.

As the sensor 200 continues to withdraw from the patient's skin and is withdrawn to the position labeled "skin line 3" in FIGS. 2A-2B, the first active sensing area 207 of the first working electrode 202 remains completely inserted, but the two proximalmost discrete sensing spots 212 of the second active sensing area 208 are withdrawn from the patient's skin. Accordingly, the ratio of the first and second output signals $(i_1/i_2)$ increases to 1.5 (i.e., 6/4), which exceeds the equilibrium value of 1. This increase in the ratio of the first and second output signals $(i_1/i_2)$ above the equilibrium value is indicative of further partial pullout of the sensor 200. Again, no correction to the output signal $(i_1)$ (e.g., output current) of the first working electrode 202 is required at this position because the first active sensing area 207 of the first working electrode 202 remains fully inserted into the patient's skin.

As the sensor 200 continues to withdraw from the patient's skin and is withdrawn to the position labeled "skin line 4" in FIGS. 2A-2B, the first active sensing area 207 of the first working electrode 202 remains completely inserted, but the three proximalmost discrete sensing spots 212 of the second active sensing area 208 are withdrawn from the patient's skin. Accordingly, the ratio of the first and second output signals $(i_1/i_2)$ increases to 2 (i.e., 6/3), which exceeds the equilibrium value of 1. This increase in the ratio of the first and second output signals $(i_1/i_2)$ above the equilibrium value is indicative of further partial pullout of the sensor 200.

As the sensor 200 continues to withdraw from the patient's skin and is withdrawn to the position labeled "skin line 5" in FIGS. 2A-2B, the proximalmost discrete sensing spot 211 of the first active sensing area 207 is withdrawn from the patient's skin and the four proximalmost discrete sensing spots 212 of the second active sensing area 208 are withdrawn from the patient's skin. Accordingly, the ratio of the first and second output signals $(i_1/i_2)$ increases to 2.5 (i.e., 5/2), which exceeds the equilibrium value of 1. This increase in the ratio of the first and second output signals $(i_1/i_2)$ above the equilibrium value is indicative of further partial pullout of the sensor 200. Additionally, because a portion (e.g., the proximalmost discrete sensing spot 211) of the first active sensing area 207 of the first working electrode 202 has been withdrawn from the patient's skin, the output signal $(i_1)$ of the first working electrode 202 has been artificially depressed and therefore needs to be corrected (i.e., the system needs to compensate for the artificially depressed output signal $(i_1)$ of the first working electrode 202 due to the partial withdrawal of the transcutaneous sensor 200 from the patient's skin). In the illustrated embodiment, the increase in the ratio of the first and second output signals $(i_1/i_2)$ to 2.5 from an equilibrium value of 1 indicates that the output signal $(i_1)$ (e.g., the output current) of the first working electrode 202 needs to be corrected by +20% to compensate for the reduction in the output signal due to the partial withdrawal of the sensor 200. That is, because one of the six discrete sensing spots 211 has withdrawn from the patient's skin, the first active sensing area 207 generates an output signal ($i_1$) that has been artificially depressed to $\frac{5}{6}$ and therefore the output signal ($i_1$) needs to be corrected by a factor of $\frac{6}{5}$ (i.e., 1.2 or 20%) to compensate for the reduction in the output signal ($i_1$) due to the partial withdrawal.

As the sensor 200 continues to withdraw from the patient's skin and is withdrawn to the position labeled "skin line 6" in FIGS. 2A-2B, the two proximalmost discrete sensing spots 211 of the first active sensing area 207 are withdrawn from the patient's skin and the five proximalmost discrete sensing spots 212 of the second active sensing area 208 are withdrawn from the patient's skin. Accordingly, the ratio of the first and second output signals ($i_1/i_2$) increases to 4 (i.e., 4/1), which exceeds the equilibrium value of 1. This increase in the ratio of the first and second output signals ($i_1/i_2$) above the equilibrium value is indicative of further partial pullout of the sensor 200. Additionally, because a portion of (e.g., the two proximalmost sensing spots 211) the first active sensing area 207 of the first working electrode 202 has been withdrawn from the patient's skin, the output signal ($i_1$) of the first working electrode 202 has been artificially depressed and therefore needs to be corrected. In the illustrated embodiment, the increase in the ratio of the first and second output signals ($i_1/i_2$) to 4 from an equilibrium value of 1 indicates that the output signal ($i_1$) (e.g., the output current) of the first working electrode 202 needs to be corrected by +50% to compensate for the reduction in the output signal due to the partial withdrawal of the sensor 200. That is, because two of the six discrete sensing spots 211 have withdrawn from the patient's skin, the first active sensing area 207 generates an output signal ($i_1$) that has been artificially depressed to $\frac{4}{6}$ and therefore the output signal ($i_1$) needs to be corrected by a factor of $\frac{6}{4}$ (i.e., 1.5 or 50%).

As the sensor 200 continues to withdraw from the patient's skin and is withdrawn to the position labeled "skin line 7" in FIGS. 2A-2B, the three proximalmost discrete sensing spots 211 of the first active sensing area 207 and all six of the discrete sensing spots 212 of the second active sensing area 208 are withdrawn from the patient's skin. Accordingly, the ratio of the first and second output signals ($i_1/i_2$) increases to infinity, which indicates pullout of the sensor 200 but does not permit correction of the first output signal of the first working electrode 202. Accordingly, in one or more embodiments, the output signal (e.g., the output current) of the first working electrode 202 may be corrected as long as the output signal of the second working electrode 203 is non-zero (i.e., as long as at least a portion of the second active sensing area 208 of the second working electrode 203 is below the patient's skin line).

Table 2 below summarizes the ratio of the first and second output signals ($i_1/i_2$) and the correction to the first output signal ($i_1$) as a function of skin position.

TABLE 2

| Skin position | $i_1/i_2$ | Implied Correction to $i_1$ |
|---|---|---|
| Skin line 1 | 1 | 0% |
| Skin line 2 | 1.2 | 0% |
| Skin line 3 | 1.5 | 0% |
| Skin line 4 | 2 | 0% |
| Skin line 5 | 2.5 | +20% |
| Skin line 6 | 4 | +50% |
| Skin line 7 | Very large | Not possible |

Although in the embodiments of the transcutaneous sensors 100, 200 illustrated in FIGS. 1A-1C and FIGS. 2A-2B a portion of the first active sensing area overlaps with at least a portion of the second active sensing area, in one or more embodiments, no portion of the first active sensing may overlap with the second active sensing area (e.g., the first and second active sensing areas of the first and second working electrodes, respectively, may be located at mutually exclusive longitudinal positions along the length of the substrate). For instance, FIGS. 3A-3B depict an embodiment of a transcutaneous sensor 300 including a first working electrode 301 having a first active sensing area 302 with a series of discrete sensing spots 303 (e.g., three discrete sensing spots) and a second working electrode 304 having a second active sensing area 305 with a series of discrete sensing spots 306 (e.g., three discrete sensing spots). In the embodiment illustrated in FIGS. 3A-3B, the first active sensing area 302 (e.g., the discrete sensing spots 303 of the first active sensing area 302) does not overlap (e.g., is longitudinally misaligned) from the second active sensing area 305 (e.g., the discrete sensing spots 306 of the second active sensing area 305). Although in the illustrated embodiment, the number of sensing spots 303 in the first active sensing area 302 is the same as the number of sensing spots 306 in the second active sensing area 305, in one or more embodiments, the number of sensing spots 303 in the first active sensing area 302 may be different than the number of sensing spots 306 in the second active sensing area 305. Additionally, in one or more embodiments, the first active sensing area 302 and/or the second active sensing area 305 may include a continuous strip (e.g., an elongated ellipse) rather than a series of discrete sensing spots.

Analyte Monitoring System

Incorporating embodiments of the present invention, analyte monitoring devices and systems include an analyte sensor having a first and second working electrode with the first active sensing area on the first working electrode offset as disclosed from the second active sensing area of the second electrode. As described, the first and second active sensing areas are positionable beneath the skin surface of the user for the in vivo detection of an analyte in a body fluid. Analyte monitoring systems are disclosed in Say et al. (U.S. Pat. No. 6,134,461) and Hoss et al., (U.S. Patent Application Publication No. 2012/0150005), the entire contents of both of which are herein incorporated by reference. Embodiments of the present disclosure include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of analyte, which may be used to infer the analyte level in the user's bloodstream. Analyte sensors may be insertable into a vein, artery, or other portion of the body containing fluid. In some embodiments, the analyte sensors may be configured for monitoring the level of the analyte over a time period which may range from seconds, minutes, hours, days, weeks, to months, or longer.

In some embodiments of the present disclosure, the analyte sensors are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time $t_0$, the rate of change of the analyte, etc. Predictive alarms may notify the user of a predicted analyte level that may be of concern in advance of the user's analyte level reaching the future predicted analyte level. This provides the user an opportunity to take corrective action.

Figure 4:
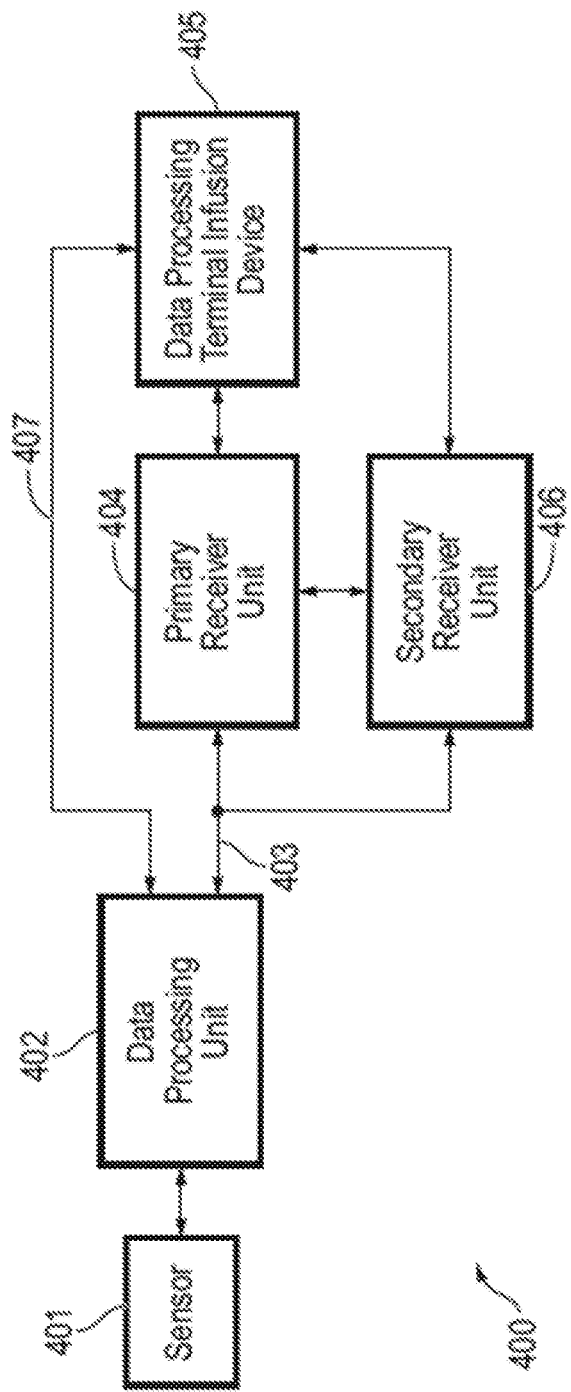
FIG. 4 shows a block diagram of an embodiment of an analyte monitoring system according to embodiments of the present disclosure.

FIG. 4 shows a data monitoring and management system such as, for example, an analyte monitoring system 400 in accordance with certain embodiments of the present disclosure. Aspects of embodiments of the present disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes as disclosed herein at the same time or at different times.

Analytes that may be monitored include, but are not limited to, glucose, lactate, 3-hydroxy butyrate, cortisol, alcohol, pyruvate, glutamate, theophylline, acetylcholine, amylase, bilirubin, cholesterol, chorionic gonadotropin, glycosylated hemoglobin (HbA1c), creatine kinase (e.g., CK-MB), creatine, creatinine, DNA, fructosamine, glucose derivatives, glutamine, growth hormones, hormones, 3-hydroxy butyrate, ketones, ketone bodies, peroxide, prostate-specific antigen, prothrombin, RNA, thyroid stimulating hormone, and troponin. Analytes also include drugs, such as, for example, antibiotics (e.g., gentamicin, vancomycin, and the like), digitoxin, digoxin, drugs of abuse, theophylline, and warfarin, may also be monitored. In some embodiments, more than one analyte is monitored, and the analytes may be monitored at the same or different times.

The analyte monitoring system 400 includes an analyte sensor 401, a data processing unit 402 connectable to the sensor 401, and a primary receiver unit 404. In some instances, the primary receiver unit 404 is configured to communicate with the data processing unit 402 via a communication link 403. In certain embodiments, the primary receiver unit 404 may be further configured to transmit data to a data processing terminal 405 to evaluate or otherwise process or format data received by the primary receiver unit 404. The data processing terminal 405 may be configured to receive data directly from the data processing unit 402 via a communication link 407, which may optionally be configured for bi-directional communication. Further, the data processing unit 402 may include a transmitter or a transceiver to transmit and/or receive data to and/or from the primary receiver unit 404 and/or the data processing terminal 405 and/or optionally a secondary receiver unit 406.

Also shown in FIG. 4 is an optional secondary receiver unit 406 which is operatively coupled to the communication link 403 and configured to receive data transmitted from the data processing unit 402. The secondary receiver unit 406 may be configured to communicate with the primary receiver unit 404, as well as the data processing terminal 405. In some embodiments, the secondary receiver unit 406 may be configured for bi-directional wireless communication with each of the primary receiver unit 404 and the data processing terminal 405. As discussed in more detail below, in some instances, the secondary receiver unit 406 may be a de-featured receiver as compared to the primary receiver unit 404, for instance, the secondary receiver unit 406 may include a limited or minimal number of functions and features as compared with the primary receiver unit 404. As such, the secondary receiver unit 406 may include a smaller (in one or more, including all, dimensions), compact housing or embodied in a device including a wrist watch, arm band, PDA, mp3 player, cell phone, etc., for example. Alternatively, the secondary receiver unit 406 may be configured with the same or substantially similar functions and features as the primary receiver unit 404. The secondary receiver unit 406 may include a docking portion configured to mate with a docking cradle unit for placement by, e.g., the bedside for night time monitoring, and/or a bi-directional communication device. A docking cradle may recharge a power supply.

Only one analyte sensor 401, data processing unit 402 and data processing terminal 405 are shown in the embodiment of the analyte monitoring system 400 illustrated in FIG. 4. However, it will be appreciated by one of ordinary skill in the art that the analyte monitoring system 400 may include more than one sensor 401 and/or more than one data processing unit 402, and/or more than one data processing terminal 405. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 400. For example, unique IDs, communication channels, and the like, may be used.

In certain embodiments, the sensor 401 is physically positioned in or on the body of a user whose analyte level is being monitored. The sensor 401 may be configured to at least periodically sample the analyte level of the user and convert the sampled analyte level into a corresponding signal for transmission by the data processing unit 402. The data processing unit 402 is capable of being coupled to the sensor 401 such that both devices are positioned in or on the user's body, with at least a portion of the analyte sensor 401 positioned transcutaneously. The data processing unit may include a fixation element, such as an adhesive or the like, to secure it to the user's body. A mount attachable to the user and mateable with the data processing unit 402 may be used. For example, a mount may include an adhesive surface. The data processing unit 402 performs data processing functions, where such functions may include, but are not limited to, filtering and encoding of data signals, each of which corresponds to a sampled analyte level of the user, for transmission to the primary receiver unit 404 via the communication link 403. In some embodiments, the sensor 401 or the data processing unit 402 or a combined sensor/data processing unit may be wholly implantable under the skin surface of the user.

In certain embodiments, the primary receiver unit 404 may include an analog interface section including an RF receiver and an antenna that is configured to communicate with the data processing unit 402 via the communication link 403, and a data processing section for processing the received data from the data processing unit 402 including data decoding, error detection and correction, data clock generation, data bit recovery, etc., or any combination thereof.

In operation, the primary receiver unit 404 in certain embodiments is configured to synchronize with the data processing unit 402 to uniquely identify the data processing unit 402, based on, for example, an identification information of the data processing unit 402, and thereafter, to periodically receive signals transmitted from the data processing unit 402 associated with the monitored analyte levels detected by the sensor 401.

Referring again to FIG. 4, the data processing terminal 405 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 405 may further be connected to a data network (not shown) for storing, retrieving, updating, and/or analyzing data corresponding to the detected analyte level of the user.

The data processing terminal 405 may include a drug delivery device (e.g., an infusion device), such as an insulin infusion pump or the like, which may be configured to administer a drug (e.g., insulin) to the user, and which may be configured to communicate with the primary receiver unit 404 for receiving, among others, the measured analyte level. Alternatively, the primary receiver unit 404 may be configured to integrate an infusion device therein so that the primary receiver unit 404 is configured to administer an appropriate drug (e.g., insulin) to users, for example, for administering and modifying basal profiles, as well as for determining appropriate boluses for administration based on, among others, the detected analyte levels received from the data processing unit 402. An infusion device may be an external device or an internal device, such as a device wholly implantable in a user.

In certain embodiments, the data processing terminal 405, which may include an infusion device, e.g., an insulin pump, may be configured to receive the analyte signals from the data processing unit 402, and thus, incorporate the functions of the primary receiver unit 404 including data processing for managing the user's insulin therapy and analyte monitoring. In certain embodiments, the communication link 403, as well as one or more of the other communication interfaces shown in FIG. 4, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 5:
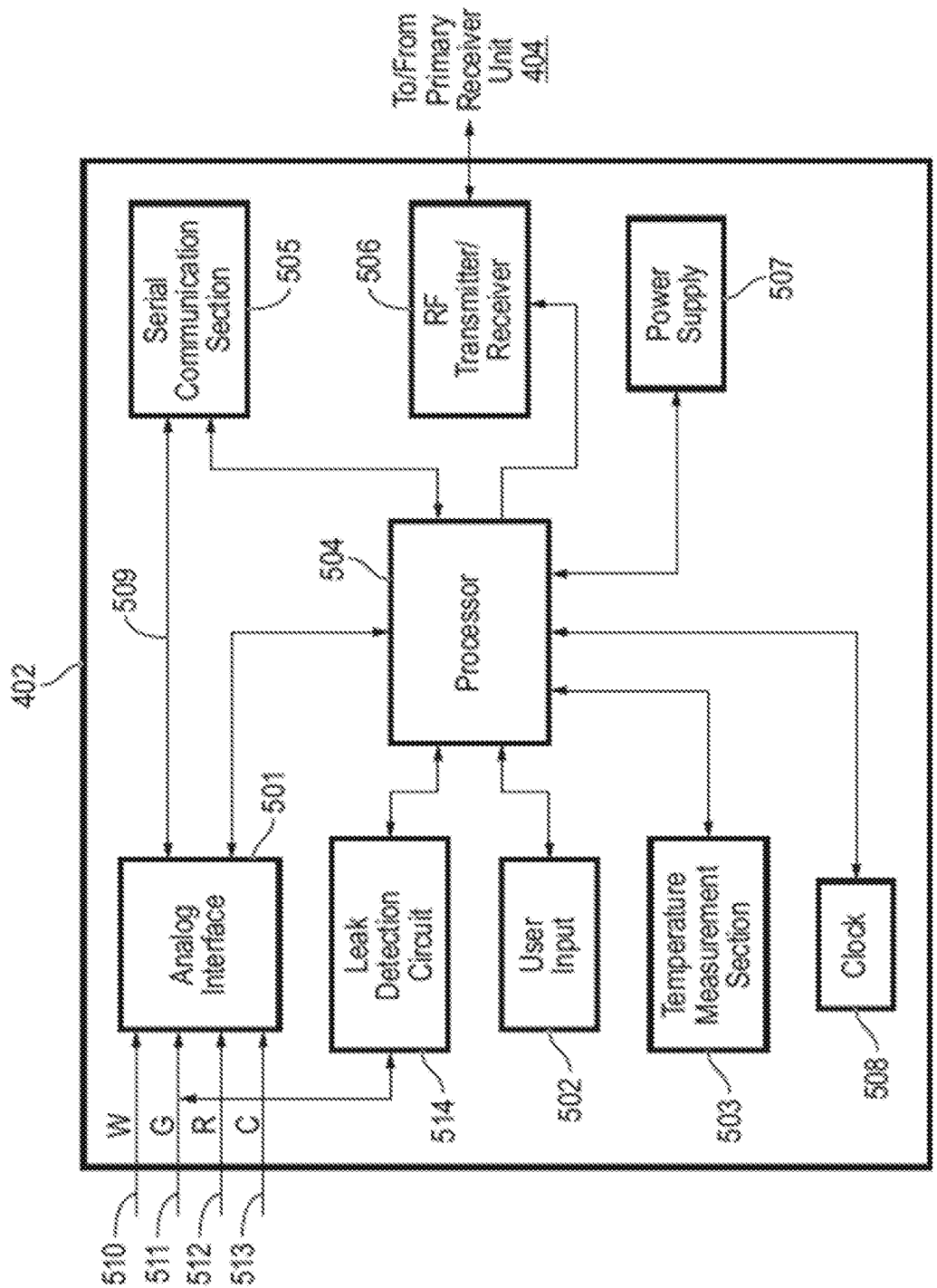
FIG. 5 shows a block diagram of an embodiment of a data processing unit of the analyte monitoring system of FIG. 4, according to embodiments of the present disclosure.

FIG. 5 shows a block diagram of an embodiment of a data processing unit 402 of the analyte monitoring system shown in FIG. 4. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 5, the analyte sensor 401 (FIG. 4) includes four contacts, three of which are electrodes: a working electrode (W) 510, a reference electrode (R) 512, and a counter electrode (C) 513, each operatively coupled to the analog interface 501 of the data processing unit 402. This embodiment also shows an optional guard contact (G) 511. Fewer or greater electrodes may be employed. For example, the counter and reference electrode functions may be served by a single counter/reference electrode. In some cases, there may be more than one working electrode and/or reference electrode and/or counter electrode, etc.

Figure 6:
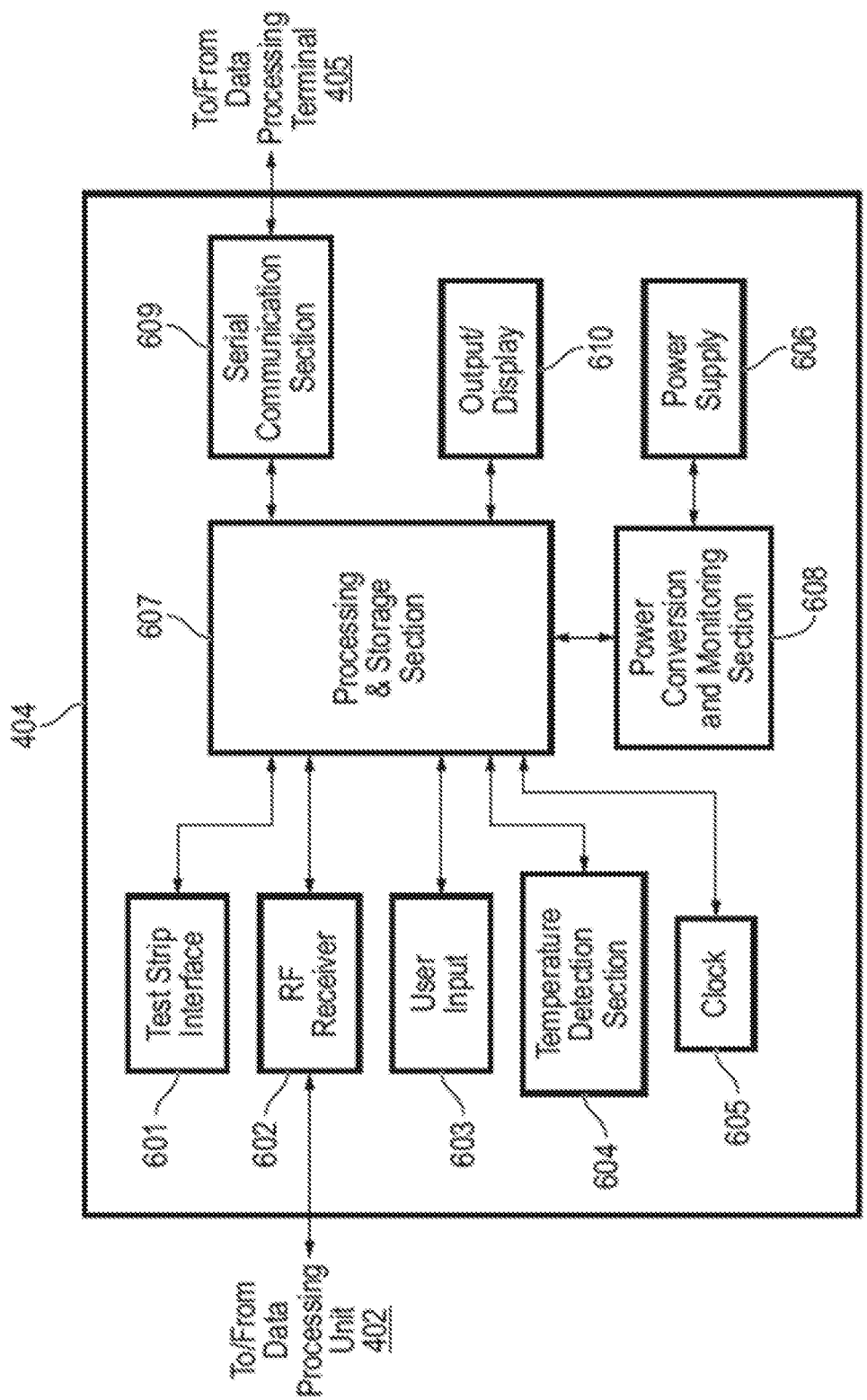
FIG. 6 shows a block diagram of an embodiment of the primary receiver unit of the analyte monitoring system of FIG. 4, according to embodiments of the present disclosure.

FIG. 6 is a block diagram of an embodiment of a receiver/monitor unit such as the primary receiver unit 404 of the analyte monitoring system shown in FIG. 4. The primary receiver unit 404 includes one or more of: a test strip interface 601, an RF receiver 602, a user input 603, an optional temperature detection section 604, and a clock 605, each of which is operatively coupled to a processing and storage section 607. The primary receiver unit 404 also includes a power supply 606 operatively coupled to a power conversion and monitoring section 608. Further, the power conversion and monitoring section 608 is also coupled to the processing and storage section 607. Moreover, also shown are a receiver serial communication section 609, and an output 610, each operatively coupled to the processing and storage section 607. The primary receiver unit 404 may include user input and/or interface components or may be free of user input and/or interface components.

In certain embodiments, the test strip interface 601 includes an analyte testing portion to receive a blood (or other body fluid sample) analyte test or information related thereto. For example, the test strip interface 601 may include a test strip port to receive an analyte test strip. The device may determine the analyte level of the test strip, and optionally display (or otherwise notice) the analyte level on the output 610 of the primary receiver unit 404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate analyte information. Glucose information obtained by an in vitro glucose testing device may be used for a variety of purposes, computations, etc. For example, the information may be used to calibrate sensor 401, confirm results of sensor 401 to increase the confidence thereof (e.g., in instances in which information obtained by sensor 401 is employed in therapy related decisions), etc.

In further embodiments, the data processing unit 402 and/or the primary receiver unit 404 and/or the secondary receiver unit 406, and/or the data processing terminal (infusion device) 405 may be configured to receive the analyte value wirelessly over a communication link from, for example, a blood analyte meter. In further embodiments, a user manipulating or using the analyte monitoring system 400 (FIG. 4) may manually input the analyte value using, for example, a user interface (for example, a keyboard, keypad, voice commands, and the like) incorporated in one or more of the data processing unit 402, the primary receiver unit 404, the secondary receiver unit 406, or the data processing terminal (infusion device) 405.

Sensor Membrane

Figure 7:
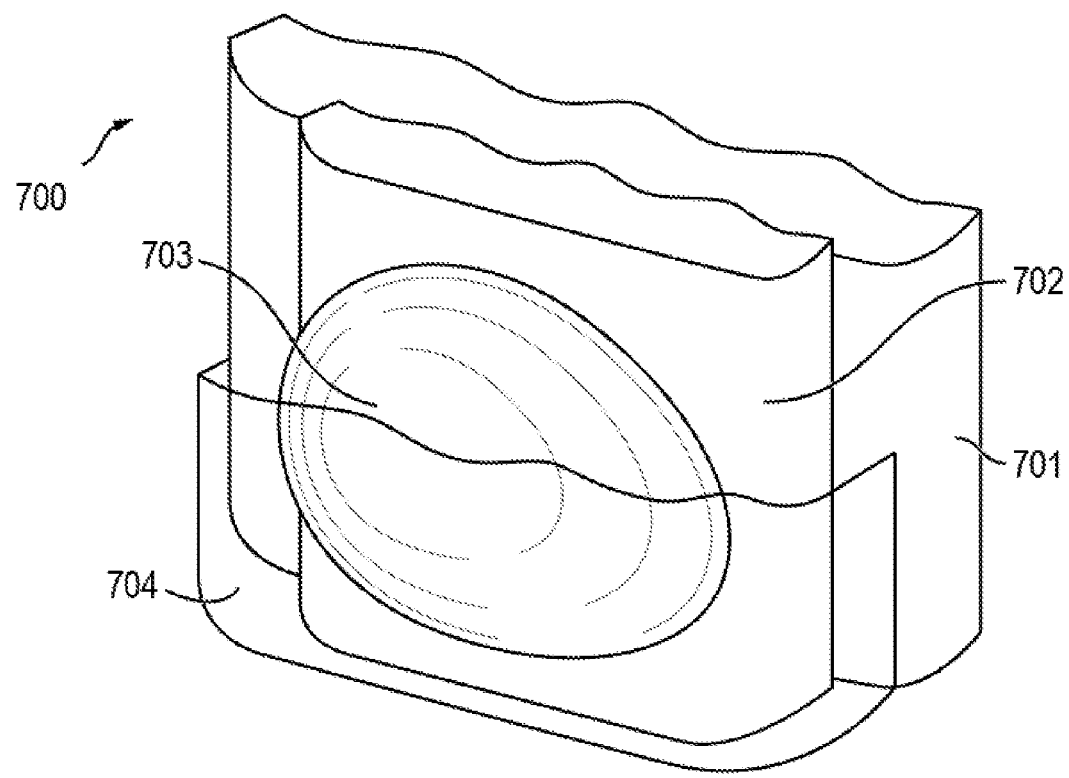
FIG. 7 shows a close-up view of the sensing area, working electrode, and substrate with an overlaying outer membrane, according to embodiments of the present disclosure.

In some embodiments of the present disclosure, with reference to FIG. 7, the sensor 100, 200, or 300 or a portion 700 of one of these sensors including a substrate 701, in which an outer membrane 704 overlays the entire sensor or at least the first and second active sensing areas (a first active sensing area 703 is shown) on the first and second working electrodes (the first working electrode 702 is shown). Electrochemical sensors are often times coated with an outer membrane 704 (e.g., a polymer membrane) in order to provide stability to the sensing reagents (e.g., the analyte-specific enzyme and redox), as well as provide mass-transport limitations, biocompatibility, and/or to prevent electrode fouling.

Accordingly, FIG. 7 depicts a close-up perspective of the outer membrane 704 overlaying a first active sensing area 703 disposed on a first working electrode 702 that is disposed on a substrate 701. As depicted, the outer membrane 704 is in the process of being overlaid. The outer membrane 704 overlays at least the entire first active sensing area (703 as shown) and the active second sensing area.

In some embodiments of the present disclosure, the membrane is composed of two components, a hydrophilic (water-loving) polymer and a crosslinker. The crosslinker attaches the polymer molecules together and anchors them to the sensing layer of the sensor. For analytes such as glucose which are found in vivo at concentrations of about 5 mM, a flux-limiting membrane is necessary to prevent electrode fouling. Examples of flux-limiting sensor membranes are disclosed, for example, in Mao et al. U.S. Pat. No. 6,932,894, the entire content of which is herein incorporated by reference.

For analytes as lower concentrations, a flux-limiting membrane could be used with increased accumulation time, for example, up to 30 minutes. Alternatively, for analytes at lower concentrations a highly permeably membrane may be used in order to maintain the natural flow of analyte to the sensing layer, while also having a membrane to increase the biocompatibility of the sensor. For example a hydrophilic membrane surface does not aggravate the body's immune system, thereby reducing the risk of inflammation and other responses that could compromise the performance of the sensor.

Analyte-Specific Enzymes and Electron Transfer Agent (Redox Mediator)

In some embodiments of the present disclosure, the sensors of the present disclosure are not designed to measure analyte directly. That is, the electrodes on the sensor are not designed to directly interact with the analyte. Accordingly, the analyte is detected by an enzyme protein that is capable of interacting directly with the analyte molecule. However, some enzymes (e.g., glucose oxidase) cannot exchange electrons directly with electrodes because their redox active sites are buried deep within the enzyme protein structure. Therefore, in order to transfer electrons between the redox active site of the enzyme and the electrodes, an electron transfer agent (i.e., a redox mediator) is used. Immobilization of the electron transfer agent and the analyte-specific enzyme on the sensing layer creates what is referred to as a "wire" as the immobilized molecules are capable of relaying electrons, and as such are "electrically wired." The analyte-specific enzyme is also referred to as a "wired enzyme." Wired enzymes are disclosed, for example, in Gregg et al., (U.S. Pat. No. 5,262,035), Say et al., (U.S. Pat. No. 6,134,461), and Hoss et al., (U.S. Patent Publication No. 2012/0150005), the entire contents of all of which are herein incorporated by reference. In some embodiments, the analyte-specific enzyme is crosslinked to the electron transfer agent.

In some embodiments of the present disclosure, electron transfer agents (e.g., redox mediators) are electroreducible and electrooxidizable ions or molecules having redox potentials (voltages) that are a few hundred millivolts above or below the redox potential (voltage) of the standard calomel electrode (SCE). In some embodiments, the electron transfer agents are not more reducing than about −150 mV and not more oxidizing than about +400 mV versus SCE. Examples of suitable redox mediators in the form of redox polymers are disclosed, for example, in Mao et al. (U.S. Pat. No. 6,605,200) the entire content of which is herein incorporated by reference.

According to embodiments of the present disclosure, an electron transfer agent is immobilized on the first and second active sensing areas on the first and second working electrodes. In some embodiments, the electron transfer agent and an analyte-specific enzyme are both immobilized on the working electrodes by any suitable means forming the active sensing areas. In some embodiments, the electron transfer agent and analyte-specific enzyme are co-immobilized onto the working electrodes with any suitable crosslinker thereby forming the active sensing areas. In some embodiments, the electron transfer agent and analyte-specific enzyme are co-immobilized with a chemical crosslinker, for example, poly (ethylene glycol) diglycidyl ether (PEGDGE).

In some embodiments of the present disclosure, an electron transfer agent for use in accumulation mode sensing includes a redox species selected from osmium, ruthenium, iron, or cobalt coupled with a polymer selected from poly (vinylpyridine), poly(thiophene), poly(aniline), poly(pyrrole), or poly(acetylene). In some embodiments, an electron transfer agent is the osmium (Os)-containing poly(vinylpyridine) redox polymer of Formula I.

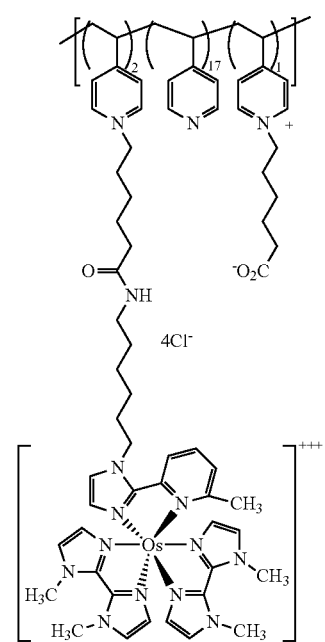

Formula I

In some embodiments of the present disclosure, the electron transfer agent may be organic, organometallic, or inorganic. Examples of organic redox species are quinones and species that in their oxidized state have quinoid structures, such as Nile blue and indophenol. Some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present disclosure because of the presence of the interfering proteins in an analyte-containing fluid. It is noted that most substituted quinones and molecules with quinoid structure are less reactive with proteins. In some embodiments, a tetrasubstituted quinone has carbon atoms in positions 1, 2, 3, and 4.

Electron transfer agents suitable for use with a dual working electrode transcutaneous sensor have structures or charges which prevent or substantially reduce the diffusional loss of the electron transfer agent. In some embodiments of the present disclosure, an electron transfer agent includes a redox species bound to a polymer which is capable of being immobilized on the sensing layer of the working electrode. The bond between the redox species and the polymer may be covalent, coordinative, or ionic. Useful electron transfer agents and methods for producing them are described in U.S. Pat. Nos. 5,264,104; 5,356,786; 5,262,035; and 5,320,725, the entire contents of all of which are herein incorporated by reference. Although any organic or organometallic redox species may be bound to a polymer and used as an electron transfer agent, in some embodiments of the present disclosure, the redox mediator is a transition metal compound or complex. In some embodiments, transition metal compounds or complexes include osmium, ruthenium, iron, and cobalt compounds or complexes. It will be recognized that many of the redox mediator species described herein may also be used, for example, without a polymeric component in an active sensing area of a sensor where leaching of the electron transfer agent is acceptable.

One type of non-releasable polymeric electron transfer agent contains a redox species covalently bound in a polymeric composition. An example of this type of mediator is poly(vinylferrocene).

Another type of non-releasable electron transfer agent contains an ionically-bound redox species. Typically, this type of mediator includes a charged polymer coupled to an oppositely charged redox species. Examples of this type of mediator include a negatively charged polymer such as Nafion (Dupont) coupled to a positively charged redox species such as an osmium, ruthenium, iron, or cobalt-coupled polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In some embodiments of the present disclosure a bound redox species is a highly charged redox species bound within an oppositely charged redox polymer.

In another embodiment of the disclosure, suitable non-releasable electron transfer agents include a redox species coordinatively bound to a polymer. For example, the mediator may be formed by coordination of an osmium or cobalt 2,2'-bipyridyl complex to poly(1-vinyl imidazole) or poly (4-vinyl pyridine).

In some embodiments of the present disclosure, the electron transfer agents are osmium transition metal complexes with one or more ligands, each ligand having a nitrogen-containing heterocycle such as 2,2'-bipyridine, 1,10-phenanthroline, or derivatives thereof. Furthermore, in some embodiments, the electron transfer agents have one or more ligands covalently bound in a polymer, each ligand having at least one nitrogen-containing heterocycle, such as pyridine, imidazole, or derivatives thereof. These preferred electron transfer agents exchange electrons rapidly between each other and the working electrodes so that the complex may be rapidly oxidized and reduced.

In some embodiments of the present disclosure, an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. In some embodiments, derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine are used. In some embodiments, derivatives of 1,10-phenanthroline for complexation with the osmium cation are 4,7-dimethyl-1,10-phenanthroline and mono-, di-, and polyalkoxy-1,10-phenanthrolines, such as 4,7-dimethoxy-1,10-phenanthroline. In some embodiments of the present disclosure, polymers for complexation with the osmium cation include polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole. In some embodiments, electron transfer agents include osmium complexed to a polymer or copolymer of poly(1-vinyl imidazole).

According to embodiments of the present disclosure, electron transfer agents have a redox potential (voltage) ranging from −100 mV to about +150 mV versus the standard calomel electrode (SCE). More specifically, the potential (voltage) of the electron transfer agent ranges from −100 mV to +150 mV. In some embodiments, the potential (voltage) ranges from −50 mV to +50 mV. In other embodiments of the present disclosure, electron transfer agents have osmium, ruthenium, iron, or cobalt redox centers and a redox potential (voltage) ranging from +50 mV to −150 mV versus SCE. While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims. Although relative terms such as "outer," "inner," "upper," "lower," and similar terms have been used herein to describe a spatial relationship of one element to another, it is understood that these terms are intended to encompass different orientations of the various elements and components of the invention in addition to the orientation depicted in the figures. Additionally, as used herein, the term "substantially," "about," and similar terms are used as terms of approximation and not as terms of degree, and are intended to account for the inherent deviations in measured or calculated values that would be recognized by those of ordinary skill in the art. Moreover, the tasks described above may be performed in the order described or in any other suitable sequence. Additionally, the methods described above are not limited to the tasks described. Instead, for each embodiment, one or more of the tasks described above may be absent and/or additional tasks may be performed. Furthermore, as used herein, when a component is referred to as being "on" another component, it can be directly on the other component or components may also be present therebetween. Moreover, when a component is component is referred to as being "coupled" to another component, it can be directly attached to the other component or intervening components may be present therebetween.

What is claimed is:

1. A method of detecting withdrawal of a transcutaneous sensor from a patient, the method comprising:
   transducing, with a first working electrode and a second working electrode of the transcutaneous sensor, an analyte in the patient into a first current output and a second current output;
   determining a current ratio of the first current output by the first working electrode of the transcutaneous sensor to the second current output by the second working electrode of the transcutaneous sensor;
   comparing the current ratio to a size ratio defined by a first size of a first active sensing area of the first working electrode to a second size of a second active sensing area of the second working electrode; and
   determining that the transcutaneous sensor has at least partially withdrawn from the patient based on the current ratio being different than the size ratio.

2. The method of claim 1, further comprising compensating for a reduction in the current output from one of the first and second working electrodes due to the partial withdrawal of the transcutaneous sensor using a difference between the current ratio and the size ratio.

3. The method of claim 1, wherein the first active sensing area has a first size and wherein the second active sensing area has a second size different than the first size.

4. The method of claim 1, wherein the first active sensing area has a first size and wherein the second active sensing area has a second size substantially equal to the first size.

5. The method of claim 1, wherein the first active sensing area comprises a first plurality of sensing spots and wherein the second active sensing area comprises a second plurality of sensing spots.

6. The method of claim 5, wherein a size of each sensing spot of the first plurality is substantially the same as a size of each sensing spot of the second plurality.

7. The method of claim 6, wherein the first plurality of sensing spots comprises a greater number of sensing spots than the second plurality of sensing spots.

8. The method of claim 1, wherein a proximalmost end of the first active sensing area is spaced apart from a distal end of a substrate by a first distance and a proximalmost end of the second active sensing area is spaced apart from the distal end of the substrate by a second distance different than the first distance.

9. The method of claim 1, wherein a distalmost end of the first active sensing area is spaced apart from a distal end of a substrate by a first distance and a distalmost end of the second active sensing area is spaced apart from the distal end of the substrate by a second distance different than the first distance.

10. The method of claim 1, wherein a longitudinally centered portion of the first active sensing area is offset from a longitudinally centered portion of the second active sensing area.

11. The method of claim 1, further comprising a reference electrode on a substrate.

12. The method of claim 11, further comprising a counter electrode on the substrate.

13. The method of claim 12, further comprising a first dielectric insulator layer between the reference electrode and the substrate and a second dielectric insulator layer between the counter electrode and the substrate.

14. The method of claim 1, wherein the first working electrode is on a first side of a substrate and the second working electrode is on a second side of the substrate opposite the first side.

15. The method of claim 1, wherein the first active sensing area and the second active sensing area comprise an analyte-specific enzyme and an electron transfer agent.

16. The method of claim 15, wherein the first active sensing area and the second active sensing area further comprise a cross linker.

17. The method of claim 15, wherein the analyte-specific enzyme is glucose oxidase.

18. The method of claim 15, wherein the electron transfer agent is a redox polymer.

19. The method of claim 1, further comprising a membrane overlaying the first and second active sensing areas.

* * * * *